United States Patent [19]

Kilgore

[11] Patent Number: 5,254,730
[45] Date of Patent: Oct. 19, 1993

[54] PRODUCTION OF AMINO ACIDS AND AMINO ACID DERIVATIVES BEARING ISOTOPIC HYDROGEN LABELS

[76] Inventor: James L. Kilgore, Worcester Foundation of Experimental Biology 222 Maple Ave., Shrewsbury, Mass. 01545

[21] Appl. No.: 820,526

[22] Filed: Jan. 14, 1992

[51] Int. Cl.$^5$ ............................................. C07C 229/00
[52] U.S. Cl. ..................................... 562/575; 560/37; 560/39; 560/154; 560/169; 560/171; 562/443; 562/444; 562/557; 562/561; 562/562; 562/571
[58] Field of Search ............... 562/560, 561, 575, 557, 562/444, 443; 560/37, 39, 154, 169, 171

[56] References Cited

U.S. PATENT DOCUMENTS

| | | | |
|---|---|---|---|
| 3,716,551 | 2/1973 | Putter | 562/561 |
| 3,972,921 | 8/1976 | Dolling | 562/560 |
| 3,976,689 | 8/1976 | Reinhold | 562/574 |

OTHER PUBLICATIONS

Lemaster, D. J. Labelled Compounds and Radiopharmaceuticals, *1982* vol. 19, 639-46.
Stein, R. Analytical Biochemistry, 1981, vol. 116, 230-6.
Rittenberg, D. J. Amer. Chem. Soc., 1940, vol. 62, 2249-50.
Kilgore, J. L. J. Chem. Soc., Perkin. Trans. I, 1991, 79-84.

*Primary Examiner*—Michael L. Shippen

[57] ABSTRACT

Amino acids and amino acid derivatives bearing isotopic hydrogen labels at both the $\alpha$- and $\beta$-positions are produced when N-substituted azomethine derivatives of carboxylic acids and carboxylic acid derivatives are hydrogenated over metal catalysts in isotopically-enriched protic solvents with molecular hydrogen.

20 Claims, No Drawings

PRODUCTION OF AMINO ACIDS AND AMINO ACID DERIVATIVES BEARING ISOTOPIC HYDROGEN LABELS

FIELD OF THE INVENTION

This invention relates to a method for introducing hydrogen isotopes or "labels", into α-amino acids for use as probes in biological- and chemical research, and for clinical testing in medicine.

BACKGROUND OF THE INVENTION

α-Amino acids play a central role in biology and are therefore of great importance in medicine. Isotopically-labeled amino acids and their derivatives have been increasingly used in biological research and in clinical testing over the last 50 years. Compounds which contain the radioactive isotope tritium ($^3H=T$) and the nonradioactive isotope deuterium ($^2H=D$) are among the most versatile and the least expensive probes available for monitoring processes which are important in biology, chemistry- and medicine. A great deal of effort has been expended to obtain specifically- deuteriated and -tritiated amino acids and numerous preparative procedures have appeared in the scientific literature. At present, large quantities of deuterium-labeled amino acids are used for nutritional testing, for labeling amino acid-derived metabolites of pharmaceuticals and agricultural chemicals, and for studies of protein structure. Conversely, compounds having less than the natural abundance level of deuterium (0.015%), by virtue of their low "background" interference, have utility in deuterium-sensitive analyses. Tritiated amino acids are widely used in biological, clinical and environmental analysis. For the purposes of this application, the term "amino acid" shall be understood to mean α-amino carboxylic acid.

Current methods for producing labeled amino acids fall into the categories of:
1) enzymatic/fermentation methodologies and
2) chemical synthesis.

In general, enzymatic/fermentation methods (1) have the advantage of producing enantiomerically pure products. The drawbacks of these methods include the difficulty purifying products from complex incubation mixtures, and the limited number of possible amino acids which can be prepared by using known enzymes and microorganisms. Microbial fermentation in the presence of a labeled biological feedstock is the method of choice or generally-labeling the protein amino acids. "General" labeling implies the replacement of all of the atoms of a chosen element in a molecule with a specified isotope. Methods of type (1) are not well suited to site-specific labeling, that is, isotopic replacement of certain atoms of a given element, but not others in the same molecule. It is difficult to find conditions which can make the complex web of metabolic processes in living cells distinguish between different atoms of a given element in the same molecule, so as to specifically-label certain positions which are of particular interest.

Each amino acid contains a number of chemically-distinct hydrogen atoms. Substitution of all-, a select group-, or only one of the hydrogen atoms in a molecule will isotopic labels may be desirable, depending on the application. When designing an isotopic probe, choices as to which isotope to introduce and which atoms to substitute will depend on the problem to be solved. Chemical syntheses (2) can be used to introduce specific labels into any desired position in a molecule, but this may be difficult and/or expensive for certain products. Desirable features in a given isotopic synthesis may include the efficient use of readily available sources of label, a minimum number of chemical reactions and manipulations, simple purification procedures, the introduction of labels into specific- or multiple positions in the molecule as desired, and the ability to recover any unused isotopically-enriched reagents.

The α-amino acids comprise a large class of compounds, many, but not all of which, are naturally-occurring. A wide variety of functional groups are present in the side-chains of known amino acids, including hydrocarbon chains and rings, ionic functionalities (e.g. $-COO-$ and $-NH_3^+$), heterocyclic rings, and groups which are substituted with halogens, sulfur, phosphorus, selenium and many other elements. Because of this diversity, the amino acids vary a great deal in their physical and chemical properties. Differences in solubility are of particular concern when attempting to implement a general method of synthesis for these compounds, therefore any such method must be able to utilize a range of solvents.

Chemical reagents which are enriched in each of the heavy isotopes of hydrogen ($^2H$ and $^3H$) are sold commercially for use as precursors in isotopic synthesis. The same group of reactions which are used to label amino acids with deuterium can also be used to introduce tritium, although the preferred methods will vary depending on the position to be labeled and the isotope to be used. Most such methods belong to one of four types:
a) alkylation of a nucleophilic glycine equivalent (e.g. anions derived from either acylaminomalonate or glycine ester imines) with a labeled alkylating agent,
b) reductive amination with an ammonia equivalent and a labeled hydride reagent (e.g. $NaCNBH_2T$)
c) exchange of an activated amino acid or acylamino acid with labeled water
d) use of labeled molecular hydrogen for addition to a suitable multiple bond (usually carbon-carbon) or for replacement of a group (halogen, sulfur function, etc.) with the hydrogen label ("hydrogenolysis").
e) exchange of a ketoacid with labeled water, followed by conversion of the ketone carbonyl to an amino group ("reductive amination").

Alkylation strategies (a) are preferred for introducing labels on sidechain groups (except for β-hydrogen isotope introduction, see below), but they require a minimum of four synthetic steps using labeled materials and are therefore poorly suited for tritium labeling. Reductive amination with labeled hydride (b) requires a relatively costly hydride reagent, gives only modest yields ($\leq 50\%$), and only introduces one label where more may be desired. Amino acids and acylamino acids can be exchanged (c) in the α-position by using either carbonyl compounds or metal ion catalysts in either strongly acidic- or strongly basic media. Labeling in both the α- and β-positions can be accomplished by using a combination of $Al^{3+}$ and pyridoxal catalysts in isotopically-enriched HCl solution (Lemaster *J. Labeled Compounds and Radiopharm.*, 1981, 18, 639), but for compounds with metal-coordinating groups on the sidechain (e.g. lysine) the exchange reaction can be slow and in all cases product must be purified from a complex reaction mixture. Molecular hydrogen (d) is an inexpensive source of label, but certain substrates for hydrogen addition are difficult to prepare (e.g. nonaromatic acylaminoacrylic acids), while preparation of other amino acid precursors, which contain hydrogenolyzable groups, is often a multistep process. The β-hydrogens of α-ketoacids will exchange under base-catalysis, and a number of reductive amination methodologies are available for converting ketoacids to amino acids. The reductive amination method to be used is subject to one serious constraint: the reaction must not result in further exchange of the β-hydrogens. In practice, this may exclude some commonly-used reductive amination procedures.

OBJECTS OF THE INVENTION

It is an object of this invention to provide a method for producing hydrogen isotope-labeled α-amino acids in a manner which overcomes several of the shortcomings of methods in the prior art.

It is an object of this invention to provide a method for producing hydrogen isotope-labeled α-amino acids in a manner which reduces the number of synthetic steps required to obtain specifically-labeled compounds.

It is an object of this invention to provide a method for producing hydrogen isotope-labeled α-amino acids in a manner which provides these products in good chemical yields and which may be used in synthetic sequences where the introduction of more than one label is desired.

It is an object of this invention to provide a method for producing hydrogen isotope-labeled α-amino acids which may be practically and economically performed on a multigram scale.

It is an object of this invention to provide a method for producing hydrogen isotope-labeled α-amino acids in a manner which permits rapid purification by avoiding the need to remove the components of enzymatic reaction mixtures or microbial fermentation broths.

It is an object of this invention to provide a method for producing hydrogen isotope-labeled α-amino acids in a manner which is suitable for introducing tritium labels, such that the number of chemical steps and manipulations which involve radioactive materials are minimized.

It is an object of this invention to provide a method for producing hydrogen isotope-labeled α-amino acids in a manner which makes efficient use of the source of isotopic label, both by proceeding with good specific isotopic incorporation and by permitting efficient recovery of the unused isotopically-enriched reagent following the reaction.

It is an object of this invention to provide a method for producing hydrogen isotope-labeled α-amino acids in a manner which makes use of unlabeled precursors which are readily available, either from commercial sources or by expedient synthetic methods.

It is an object of this invention to provide a method for producing hydrogen isotope-labeled α-amino acids in a manner which may be used to prepare amino acids which do not occur naturally and cannot be easily synthesized enzymatically or by fermentation.

In most cases, the object of this invention is to introduce heavy hydrogen isotopes into positions on the product molecules where one or more of the corresponding positions on the precursors were not enriched with those same heavy isotopes.

These and other important objects will be apparent the description of the invention which follows.

BACKGROUND ART

A process for producing glutamic acid by reduction of α-ketoglutaric acid with deuterium gas in isotopically-unenriched aqueous ammonia was reported previously (Rittenberg, *J. Am. Chem. Soc.*, 1940, 62, 2249). The product was labeled mostly at the β-position, with much less deuterium appearing at the α-position. A procedure for preparing β-tritiated lysine by β-exchange of a related ketoacid with TOH, followed by oxime formation and hydrogenation gave the expected labeled product, but only with low specific activity (Stein *Anal. Biochem.*, 1981, 116, 230). It is clear from the design of the Stein procedure that the hydrogenation reaction was not expected to disturb the β-tritium label, which had been introduced in the previous step. This appears to have been the general expectation of the chemical community at that time. No mention was made of the fact that the specific activity was low (<2% of the theoretical maximum), so no attempt was made to explain the problems with the procedure. Prior to 1989 (the date of this invention) these two papers appear to be the only work in the open literature which deal with the preparation of β-hydrogen labeled amino acids by hydrogenation of nonolefinic precursors in the ketoacid oxidation state.

Solid-phase labeling procedures are also known in which oxime acids and other amino acid precursors are coated onto the surface of catalysts for reduction with isotopically-enriched hydrogen gas.

SUMMARY OF THE INVENTION

The present invention comprises a method for producing hydrogen isotope-labeled α-amino acids and their derivatives from N-substituted azomethine derivatives of carboxylic acids and of carboxylic acid equivalents. Catalytic reduction of the azomethine substrates in labeled protic solvents results in labeling of all β-hydrogens as well as the α-hydrogen in the products. The label is derived from a pool of exchangable hydrogens which includes the protic solvent, molecular hydrogen used in the reduction and all readily exchangable hydrogens which are present on the substrate. The processes of hydrogen exchange between solvent, molecular hydrogen and the β-hydrogens of the substrate are dependent upon the hydrogenation catalyst.

For the purposes of this discussion, "carboxylic acid equivalents" shall be understood to include carboxylic acids; their salts; their esters with alcohols, phenols and thiol derivatives; and N-unsubstituted- and N-substituted carboxamides, including those amides which are formed with amino acid amino groups. The term "N-substituted azomethines" shall be understood to include compounds containing the >C=N—X moiety, where X may be hydroxyl, alkoxy (including benzyloxy and allyloxy), aryloxy, acyloxy, unsubstituted- and substituted amino groups and any other functional group which can undergo the exchange-reduction process described herein. These definitions include any compounds described above when they bear isotopic labels of hydrogen or of other elements (especially C,N,S,P,Se, halogen) which may be present in the products.

For the purposes of this discussion, the term "isotopically-enriched", in the context of hydrogen isotopes, is assumed to mean that a higher fraction of a heavy isotope of hydrogen ($^2H$ or $^3H$) is present than would be present in a normal sample of the same chemical substance which has not been artificially enriched in the heavy isotope. Similarly, "isotopically-depleted" shall be understood to means that the fraction of heavy hydrogen isotopes has been artificially-reduced below the normal "background" level, or "natural abundance" of the heavy isotope. Since both isotopically-enriched and isotopically-depleted compounds are of commercial interest, it is convenient to expand upon the conventional definition of the word "label". For purposes of this discussion, any compound, the isotopic composition of which has been artificially altered, shall be termed "labeled" and any detectable process which alters isotopic composition shall be termed a "labeling process".

For purposes of this discussion, the term "molecular hydrogen" shall be understood to include hydrogen of any possible isotopic composition ($^1H_2$, $^1H^2H$, $^2H_2$, $^1H^3H$, $^2H^3H$ or $^3H_2$), which may be utilized in the form of hydrogen gas, or of hydrogen generated within a reaction mixture by chemical reactions or of hydrogen stored in a solid matrix (such as a HY-STOR® alloy) to be released directly into a reaction mixture.

For purposes of this discussion, the term "protic solvent" shall be understood to include any solvent containing X-H bonds, where X is one of the "heteroatoms" oxygen or nitrogen. "Heteroatom"-bound hydrogens of protic solvents which are used in the process of the invention described here may, and usually do, include heavy isotopes of hydrogen. In general, one of the most important labeling processes is that of isotopic exchange, where atoms of the same element, but of different isotopic character, are interchanged between separate molecules. It is a general property of protic solvents that the heteroatom-bound hydrogen atoms undergo facile exchange with heteroatom-bound hydrogens in other chemical substances. Such exchange may be either spontaneous, or it may be catalyzed by acids or bases. The ease with which "heteroatom"-bound hydrogens exchange stands in contrast to the typically slow- or often nonexistent exchange of hydrogens bound to carbon. Only the carbon-bound hydrogens of amino acids are sufficiently stable to exchange with their chemical environment to be useful as isotopic probes.

For purposes of the present discussion, the term "metal catalyst" shall be understood to include solid metals, metal alloys and other metal-derived compounds, including oxides and hydroxides), as well as coordination complexes of metal ions which are known to serve as hydrogenation catalysts, whether in pure form, supported on inert matrices or in solution.

This invention comprises a method for producing α-amino acids and their derivatives which are labeled with hydrogen isotopes in the α- and β-positions, and which includes the following steps: 1) mixing a metal catalyst and a protic solvent of a specified isotopic composition; 2) combining the catalyst-solvent mixture with an α-(N-substituted) azomethinecarboxylic acid equivalent; and 3) introducing a source of molecular hydrogen at a suitable pressure so as to effect the azomethine reduction concurrent with isotopic exchange of the β-hydrogens of the carboxylic acid equivalent, the molecular hydrogen and the solvent.

In preferred embodiments, the carboxylic acid equivalent is either a free carboxylic acid, a salt of a carboxylic acid, an alkyl- or aryl ester, or a carboxamide with- or without N-substituents. In highly preferred embodiments for the preparation of free amino acids, the carboxylic acid equivalent is either the free acid or a salt of the free acid.

In preferred embodiments, the azomethine N-substituent is hydroxyl, alkoxy, aryloxy, acyloxy, amino, alkylamino, arylamino or (carboxyalkyl)amino. In highly preferred embodiments for the preparation of free amino acids, the N-substituent is either hydroxyl or alkoxy.

In preferred embodiments, the metal catalyst is either a platinum group metal, including Pt, Pd, and Ni, cobalt, or compounds, salts, oxides or hydroxides derived from these metals. In highly preferred embodiments, the metal catalyst is hydrogen-reduced platinum oxide (hereafter "platinum black").

In preferred embodiments, the protic solvent used in this method is (with appropriate isotopic enrichment or depletion) water, an alcohol, a carboxylic acid, ammonia, a primary or secondary amine, or a carboxamide with either one or no N-substituents. In highly preferred embodiments, the protic solvent is isotopically-enriched water ($D_2O$, HOT or $T_2O$). The method of this invention may also include the use of additives, such as other solvents, both protic or nonprotic, or else acids or bases to alter the pH of the mixture and thereby help to solubilize the reduction substrate. Solid dispersants, such as activated charcoal, diatomaceous earth or silica, which are themselves inert to the reaction conditions, constitute another useful class of additives. Such solid additives are useful in order to maintain a free-flowing suspension within the reaction mixture and to prevent mixtures which contain partially-dissolved substrates and/or products from caking and preventing complete reaction.

The process described here has several unique advantages for the production of labeled amino acids:

Product amino acids and their derivatives can be produced in single-step procedures from readily available unlabeled precursors. Thus commercial ketoacids or their salts can be combined with hydroxylamine derivatives, hydrazines, or suitable substituted amines in isotopically-enriched solvent with a catalyst and reduced in situ to give the desired products. Oxime-containing substrates can also be prepared by nitrosation from readily-available non-ketoacid precursors, such as substituted malonic acids, malonate esters and β-ketoesters. Malonates, in particular, are generally less expensive than ketoacids, and simple syntheses of substituted malonates are known which incorporate a wide range of both natural and unnatural amino acid sidechains into the substrates.

The least expensive, most convenient and safest sources of label (e.g. $D_2O$, TOH, EtOD, EtOT, etc.) can be used for this method. For many possible substrates, purification requires only catalyst removal and evaporation of solvent. The low cost of the materials and lack of need for specialized apparatus make large scale synthesis more practical than with previous methods. The isotopically-enriched solvent can be easily recovered after the reaction (slightly depleted in isotopic content), because it is often not necessary to introduce solutes other than the substrate into the reaction mixture. When $D_2O$ is the only solvent, recovery by lyophilization of the filtered reaction mixture gives efficient recovery of the enriched solvent, which may then either be reprocessed to enhance its enrichment, be used for pre-exchange of other substrates in order to enhance the isotopic enrichment of the corresponding products or else be used as is for further reductions where products with lower isotopic enrichments are acceptable.

Most reductions can be performed at atmospheric pressure, avoiding the need for specialized apparatus. For laboratory preparations, a septum-sealed round-bottom flask is used with hydrogen introduction from a volume-measuring manifold or from a gas-filled balloon. The process is suitable for producing highly radioactive tritiated substrates, since few manipulations are required and pressure containment is not necessary.

Following their preparation by this process, the labeled products can be modified by well known procedures to give either more or fewer labeled positions as desired. Examples of such processes include selective α-exchange with unlabeled aqueous solutions to remove an α-label, and acid-catalyzed exchange (DCl/$D_2O$) to label exchangable sidechain groups such as the γ-hydrogens of glutamic acid or the 3'- and 5'-hydrogens of tyrosine. By using deuterium-depleted water as the protic solvent, the method of this invention may also be used to make amino acids with lower-than-natural abundance deuterium levels. Such compounds may be of use for reducing the background deuterium in measurements which make use of deuterium detection. A possible application would be the use of deuterium-depleted amino acids in the preparation of peptides or proteins, which are selectively deuterium-enriched at other amino acid residues, for analysis by $^2H$ NMR or mass spectrometry.

Labeled products bearing substituents on the α-amino group and on the carboxylic acid equivalent group are accessable by this process. When hydrogenation is conducted out in acetic acid containing acetic anhydride, oximes are converted to N-acetyl amines. When α-benzyloxy-imino amides of amino acids are hydrogenated, dipeptides are produced. Extension of the synthesis to tri- and higher peptides could provide labeled analogs of a number of medically-important peptide drugs. The acetylamino acids are of particular interest because they can be enzymatically resolved to give optically-pure L-amino acids.

The inventor has discovered that the hydrogenation of α-oximino acids and related compounds results in complete exchange of β-deuterium atoms of the substrate with protic solvents (Kilgore *J. Chem. Soc., Perkin Trans.* I, 1991, 79). When deuteriated oxime acid Ia was hydrogenated in isotopically-unenriched water, unlabeled amino acid IIa was obtained. In the absence of catalyst and hydrogen, no exchange of the β-hydrogen atoms of the unlabeled oxime-acid Ib was observed in $D_2O$ at a variety of temperatures and pH values. When Ib was hydrogenated in $D_2O$—$C_2H_5OH$ over platinum black and in the same solvent over 10% platinum on carbon, deuterium was observed in the α- and the β-positions of the product IIb by deuterium NMR. Proportionately less label appeared in the β-position of the sample produced using 10% platinum on carbon. The NMR spectra showed no evidence for labeling beyond the β-carbon of the products. Thus the regiospecific, catalyst-dependent labeling of amino acids during hydrogenation of soluble azomethine substrates, using the solvent as the source of label, was established.

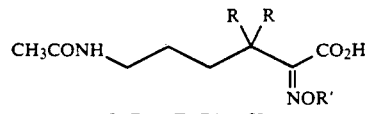

Ia R = D, R' = H;
Ib R = H, R' = H;
Ic R = D, R' = $C_6H_5CH_2$

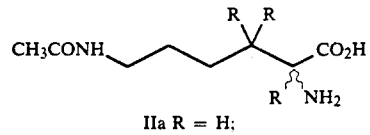

IIa R = H;
IIb R = D

The reactions which comprise the labeling process may be described by equations 1 and 2:

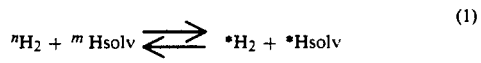

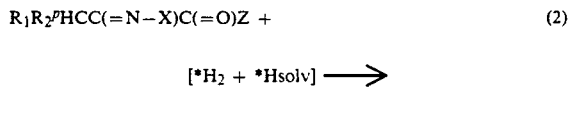

[n, m, p = 1,2 or 3 and may represent more than one isotope where more than one is present in a single molecule, i.e. $^nH_2$ can include the molecule $^1H^3H$; *H = hydrogen atom in exchanged solvent, substrate and molecular hydrogen pool; *Hsolv = protic solvent exchanged with mobile hydrogen pool; X = azomethine substituent; X' = *H or azomethine substituent after reduction; Z = carbonyl substituent before reduction; Z' = carbonyl substituent after reduction; $R_1$, $R_2$, $R_1'$, $R_2'$ = $^mH$, *H, alkyl, aryl, heteroaryl, acyl, alkoxy. —CN, carboxy, carboalkoxy, aminoalkyl, $R_3S(=O)_r$alkyl-; r = 0, 1 or 2]

"Label" hydrogens are introduced from the exchangable pool into the α- and β-positions of the product ($R_1'$, $R_2'$, $^qH$). Thus, by using a limited quantity of either labeled- or unlabeled molecular hydrogen and an excess of isotopically-enriched solvent (e.g. $D_2O$, TOH), 2, 3 or 4 positions on the product molecule backbone may become labeled, depending on the number of hydrogen atoms on the substrate β-carbon. Further labeling may occur if reducable and/or exchangable groups are present in the side chain of the substrate. Examples include cyano groups which can either remain unchanged, become reduced to labeled primary amines or become labeled while condensing with other amines.

A catalyst is required for this process. Platinum has been found to be effective both in pure form as well as when it is supported on inert matrices. Catalysis of protic solvent hydrogen/*$H_2$ exchange by the "platinum metals" (platinum, palladium and nickel); by $Co(CN)_6^{2-}$; and by coordination compounds of ruthenium-, osmium-, rhodium- and iridium is well documented. Azomethine reduction has also been described with the platinum metals, with $Co(CN)_6^{2-}$, and with other catalysts. A suitable catalyst for the proposed invention must catalyze both processes.

The solvent, molecular hydrogen and any exchangable hydrogens of the substrate (including the β-hydrogens, —OH, —NH and —SH groups) provide a pool of mobile hydrogens which may be incorporated into the product, which then is stable to further exchange. It may be calculated, by summing all sources of hydrogens available for exchange, that if the substrate is present in normal concentrations (i.e. <2 molar) in undiluted water, simple alcohols or ammonia, that the largest mole fraction of mobile hydrogens will derive from the solvent. Unlabeled hydrogen atoms both in the gaseous hydrogen and in the exchangeable positions on the substrate serve to dilute the label, thus the use of isotopically-enriched hydrogen gas and previously isotope-exchanged substrate gives rise to a higher isotopic enrichment in the product than if the solvent is the only source of label. Isotopic hydrogen is introduced from the exchangable pool into the $\beta$-position of the product (*H, $R_1'$, $R_2'$) by a mechanism which is not clearly understood. An imine-enamine tautomerization, enamine reduction sequence may rationalize the observations (Kilgore *J. Chem. Soc., Perkin Trans. I,* 1991, 79), but the claims made here do not rely on a particular interpretation of the chemical mechanisms.

While the principles of this invention have been described in connection with certain specific embodiments, it should be understood that the descriptions are made only by way of examples and are not intended to limit the scope of the invention itself. For example, a number of functional groups, such as orthoesters, orthoamides, thionoesters and thionoamides, could also serve as carboxylic acid equivalents. Similarly, sulfur-substituted azomethine compounds, including alkylthio-, arylthio-, sulfinyl and sulfonylimines may also undergo the reactions described. Substrates which are temporarily attached to solid supports, such as polypeptides or oligonucleotides which are attached to such supports during solid-phase synthesis, may be incorporated into azomethinecarboxylic acid equivalent structures and which are reduced in the presence of soluble metal catalysts. Amines or anilines which are present as solvents or additives may be used to condense with the azomethine functionality and undergo reduction so as to produce N-alkyl- or N-arylamino acid derivatives. Reaction of side chain groups with the reduced azomethine functionality is a potential route to cyclic amino acids. Thus a side chain cyano group may both undergo reduction and cyclize onto the $\alpha$-amino group formed in the reaction (or vice versa) to give cyclic amino acids with labeling at both carbons which are attached to nitrogen. Another likely use of the process would be to permit tritium labeling in protic solvents which are expensive or difficult to obtain in tritiated form (e.g. tert-butyl alcohol), by allowing tritium gas to equilibrate with the solvent and substrate in the presence of a suitable catalyst.

The following examples are given to represent several of the possible ways in which the invention may be implemented. These examples are presented by way of illustration only, and should not be construed so as to limit the scope of the invention as described in the claims which follow thereafter.

EXAMPLES OF THE INVENTION

Labeled amino acid derivatives II and IV are prepared by the following generalized protocol:

An azomethinecarboxylic acid equivalent (I or III) is combined with a mixture of a protic solvent a suitable metal catalyst, and appropriate additives as shown in the table which follows, and the resulting mixture is combined with molecular hydrogen at a pressure sufficient to effect reduction of the azomethine moiety. When the reaction is complete, the catalyst and solvent are removed and the product is isolated.

| Azomethinecarboxylic Acid Equivalent | Protic Solvent(s) | Catalyst | Molecular Hydrogen | Additive(s) | Product[a] |
|---|---|---|---|---|---|
| $Ib^b$ | $D_2O + C_2H_5OH$ | $Pt^c$ | $H_2$ | charcoal | $IIb^b$ |
| $Ic^b$ | $H_2O$ | Pt | $H_2$ | charcoal | $II^b$ |
| IIIa | $D_2O$ | Pd/C | $H_2$ | — | IVa |
| IIIb | $D_2O$ | Pt | $H_2$ | $(CH_3OCH_2)_2$, charcoal | IVb |
| IIIc | $D_2O$ | Pt | $H_2$ | $Na_2CO_3$, charcoal | IVc |
| IIId | TOH | $Pt/C^e$ | $H_2$ | $(CH_3OCH_2)_2$, charcoal | IVd |
| IIIe-i, V | f | g | $H_2$ or $D_2$ | h | IVe-i, IVa |

[a] No labels on O or N are indicated on products
[b] see Summary
[c] platinum black (hydrogenated $PtO_2$)
[d] palladium supported on carbon
[e] platinum supported on carbon
[f] selected as appropriate from $D_2O$, $H_2O$, $C_2H_5OD$, $CH_3CO_2D$, and $ND_4OD$.
[g] selected as appropriate from Pt, Pd/C, Raney Ni, $^2$-Co(CN)$_5$.
[h] selected as appropriate from charcoal, $(CH_3OCH_2O)_2$, $CH_3CN$, DCl, $CH_3CO_2Na$ and $Na_2CO_3$.

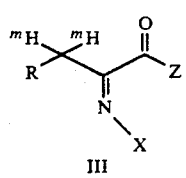

III

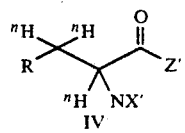

IV

-continued

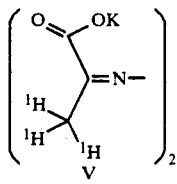

III a) R = $^1$H, X = Z = OH, m = 1
   b) R = C$_6$H$_5$, X = Z = OD, m = 2
   c) R = HO$_2$CCH$_2$, X = Z = OH, m = 1
   d) R = C$_6$H$_5$CH$_2$O, X = OH, Z = OCH$_3$, m = 1
   e) R = NC(CH$_2$)$_2$, X = OH, Z = OC$_2$H$_5$ m = 1
   f) R = CH$_3$S(=O)CH$_2$, X = Y = OH, m = 1
   g) R = $^1$H, X = N(CH$_2$)$_3$, Z = OC$_2$H$_5$ m = 1
   h) R = $^1$H, X = C$_2$H$_5$OC(=O)NH, Z = OCH$_3$, m = 1
   i) R = KO$_2$C, X = OCH$_3$, Z = CH(C$_6$H$_5$CH$_2$)CO$_2$CH$_3$, m = 1
IV a) R = $^n$H, X' = H, Z' = OH, n = 2
   b) R = C$_6$H$_5$, X' = H, Z' = OH, n = 2
   c) R = NaO$_2$CCH$_2$, X' = H, Z' = OH, n = 2
   d) R = C$_6$H$_5$CH$_2$O, X' = H, Z' = OCH$_3$, n = 3
   e) H$_2$NC$^n$H$_2$(CH$_2$)$_2$, X' = H, Z' = OC$_2$H$_5$ n = 2 (.HCl)
   f) R = CH$_3$S(=O)CH$_2$, X' = H Z' = OH, n = 2
   g) R = $^n$H, X' = H, Z' = OC$_2$H$_5$, n = 2 (.HCl)
   h) R = $^n$H, X' = H, Z' = OCH$_3$, n = 2
   i) R = HO$_2$C, X' = H, Z' = CH(C$_6$H$_5$CH$_2$)CO$_2$CH$_3$, n = 2

I claim:

1. A method for synthesizing α-amino acids, and derivatives thereof, which bear hydrogen isotopes on the α- and β-carbons by a process comprising:
   preparing a mixture consisting of a metal catalyst and a protic solvent;
   combining an α-(N-substituted azomethine)-substituted carboxylic acid equivalent with the catalyst-solvent mixture, said carboxylic acid equivalent being a compound selected from the group consisting of carboxylic acids, their salts, their esters with alcohols, phenols and thiol derivatives, and N-unsubstituted- and N-substituted carboxamides, including those amides which are formed with amino acid amino groups;
   introducing a source of molecular hydrogen at a pressure sufficient to effect the reduction of the azomethine double bond, concurrent with isotopic exchange of the substrate β-hydrogens with the protic solvent and molecular hydrogen.

2. The method of claim 1, wherein the metal catalyst is selected from the group consisting of the platinum metals, cobalt, and salts, oxides, hydroxides, sulfides and coordination compounds thereof.

3. The method of claim 2, wherein the metal catalyst is platinum black.

4. The method of claim 1, wherein the protic solvent is selected from the group consisting of water, alcohols, ammonia, carboxlic acids, mono-N-substituted carboxamides, N-unsubstituted carboxamides, primary amines, secondary amines, and mixtures thereof, said solvent having an isotope of hydrogen bound to a heteroatom.

5. The method of claim 4, wherein the heteroatom-bound hydrogen isotope is deuterium.

6. The method of claim 5, wherein the solvent is deuterium oxide.

7. The method of claim 4, wherein the heteroatom-bound hydrogen isotope is tritium.

8. The method of claim 7, wherein the solvent is tritiated water.

9. The method of claim 1, wherein the carboxylic acid equivalent is selected from the group consisting of a free carboxylic acid, an acid salt, an alkyl ester and an aryl ester of a carboxylic acid.

10. The method of claim 7, where the azomethine N-substituent is selected from the group consisting of hydroxyl, alkoxyl, amino, alkylamino, arylamino, acylamino, and (N-)imino.

11. The method of claim 10, where the N-substituent is hydroxyl.

12. The method of claim 10, where the N-substituent is alkoxy.

13. The method of claim 1, further comprising the addition of a nonprotic solvent to solublize the substrate, product and metal catalyst mixture during the reaction.

14. The method of claim 1, further comprising the addition of an inert solid dispersant to maintain a free-moving suspension within the mixture of substrate, product and metal catalyst during the reaction.

15. The method of claim 1, further comprising the adjustment of solvent pH to solublize the substrate, product and metal catalyst mixture during the reaction.

16. The method of claim 1, where, in addition to the protic solvent, the substrate is isotopically enriched in order to maximize isotopic enrichment of the product.

17. The method of claim 1, where, in addition to the protic solvent, the molecular hydrogen is isotopically enriched in order to maximize isotopic enrichment of the product.

18. The method of claim 1, where, in addition to the protic solvent, both the substrate and the molecular hydrogen are isotopically enriched in order to maximize isotopic enrichment of the product.

19. The method of claim 1, where a protic solvent, which is depleted in an isotope of hydrogen, is used in the reduction in order to produce compounds with lower levels of said isotope than were present in the precursors.

20. The method of claim 1, where the azomethinecarboxylic acid equivalent contains isotopic labels of elements which are selected from the group consisting of C, N, S, P, Se and halogen, such that said labels appear in the product in the corresponding positions.

* * * * *